United States Patent
Van Dooren et al.

(10) Patent No.: US 9,398,873 B2
(45) Date of Patent: Jul. 26, 2016

(54) METHOD OF OBTAINING A DESIRED STATE IN A SUBJECT

(75) Inventors: Marieke Van Dooren, Eindhoven (NL); Maria Estrella Mena Benito, Eindhoven (NL); Mark Thomas Johnson, Eindhoven (NL); Richard Godefridus Cornelis Van Der Wolf, Eindhoven (NL); Franciscus Antonius Maria Van Der Meijden, Eindhoven (NL)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 1605 days.

(21) Appl. No.: 12/994,161

(22) PCT Filed: Jun. 3, 2009

(86) PCT No.: PCT/IB2009/052335
§ 371 (c)(1),
(2), (4) Date: Jan. 10, 2011

(87) PCT Pub. No.: WO2009/147625
PCT Pub. Date: Dec. 10, 2009

(65) Prior Publication Data
US 2011/0172500 A1    Jul. 14, 2011

(30) Foreign Application Priority Data
Jun. 6, 2008   (EP) ..................................... 08157718

(51) Int. Cl.
G06F 19/00   (2011.01)
A61B 5/00    (2006.01)
A61B 5/16    (2006.01)
A61B 5/053   (2006.01)

(52) U.S. Cl.
CPC .. *A61B 5/16* (2013.01); *A61B 5/486* (2013.01); *A61B 5/7264* (2013.01); *G06F 19/3431* (2013.01); *A61B 5/0533* (2013.01)

(58) Field of Classification Search
None
See application file for complete search history.

(56) References Cited

U.S. PATENT DOCUMENTS

| | | | | |
|---|---|---|---|---|
| 4,173,217 A | | 11/1979 | Johnston | |
| 4,461,301 A | * | 7/1984 | Ochs | 600/301 |
| 5,377,100 A | * | 12/1994 | Pope et al. | 600/545 |
| 5,800,337 A | | 9/1998 | Gavish | |
| 6,026,322 A | * | 2/2000 | Korenman et al. | 600/547 |
| 6,067,468 A | | 5/2000 | Korenman et al. | |

(Continued)

OTHER PUBLICATIONS

Ghoniem et al: "Practical Guide to Female Pelvic Medicine", Book, Taylor & Francis Publishers, 2006, p. 207.

(Continued)

*Primary Examiner* — Gary Jackson
*Assistant Examiner* — Davin K Sands (57) ABSTRACT

A method of obtaining a desired state in (22) a subject comprises measuring one or more physiological parameters of the subject (12), calculating, using the measured parameter(s), a value (38), determining if the calculated value (38) is to be modified, modifying the calculated value, if the determination is that the value is to be modified, and generating an output to the subject, the output being in proportion to the modified value (40). The step of modifying the calculated value, if the determination is that the value is to be modified,—can comprise accessing a modification scheme and modifying the calculated value according, to the modification scheme. One method of modifying the calculated value comprises amplifying the calculated value.

8 Claims, 6 Drawing Sheets

(56) References Cited

U.S. PATENT DOCUMENTS

| | | |
|---|---|---|
| 6,450,820 B1* | 9/2002 | Palsson et al. .................. 434/236 |
| 2002/0128540 A1* | 9/2002 | Kim et al. ....................... 600/301 |
| 2003/0067486 A1 | 4/2003 | Lee et al. |
| 2004/0117212 A1 | 6/2004 | Kong et al. |
| 2004/0230549 A1* | 11/2004 | Freer et al. ....................... 706/61 |
| 2004/0249258 A1* | 12/2004 | Tupin et al. ..................... 600/407 |
| 2005/0137503 A1 | 6/2005 | Hori et al. |
| 2005/0154251 A1* | 7/2005 | Martynenko et al. ........... 600/27 |
| 2005/0154264 A1 | 7/2005 | Lecompte et al. |
| 2005/0234292 A1 | 10/2005 | Faulkner et al. |
| 2005/0288601 A1* | 12/2005 | Wood et al. ..................... 600/513 |
| 2006/0155576 A1* | 7/2006 | Deluz ............................... 705/2 |
| 2006/0217615 A1* | 9/2006 | Huiku et al. ..................... 600/484 |
| 2006/0224046 A1 | 10/2006 | Ramadas et al. |
| 2006/0270897 A1 | 11/2006 | Homer |
| 2007/0010723 A1* | 1/2007 | Uutela et al. .................... 600/301 |
| 2008/0012701 A1* | 1/2008 | Kass et al. .................. 340/539.11 |
| 2008/0146334 A1* | 6/2008 | Kil .................................. 463/36 |
| 2008/0242955 A1* | 10/2008 | Uutela et al. .................... 600/301 |
| 2009/0093686 A1* | 4/2009 | Hu et al. .......................... 600/300 |
| 2009/0105550 A1* | 4/2009 | Rothman et al. ............... 600/300 |
| 2009/0270170 A1* | 10/2009 | Patton ............................ 463/36 |

OTHER PUBLICATIONS

Shugrina et al: "Empathic Painting Interactive Stylization Using Observed Emotional State"; Proceedings 4th Intl. Symposium on Non-Photorealistic Rendering and Animation (NPAR 2006), p. 87-96, ACM Press.

Scherer: "Vocal Communication of Emotion: A Review of Research Paradigms"; Speech Communication 40 (2003),pp. 227-256.

* cited by examiner

METHOD OF OBTAINING A DESIRED STATE IN A SUBJECT

FIELD OF THE INVENTION

This invention relates to a method of, and system for, obtaining a desired state in a subject.

BACKGROUND OF THE INVENTION

The study of bio-feedback is already an established research discipline. Bio-feedback systems exist, which are comprised of one or more sensors, for example sensors for galvanic skin response, local skin temperature, heart rate and heart rate variability, respiration, electromyography, electro-encephalography etc. The aim of these systems is to extract certain physiological parameters out of the raw sensor signals that can, in this case, be interpreted in terms of emotional experience of the subject. The ongoing emotional experience can then be fed back to the user, preferably in real time, such that the user gets information about their state and can try to learn to control their bodily reactions and consequently also their emotions. Recently, the use of bio-feedback in lifestyle applications has become popular, for example, the introduction of massage devices with sensors, such as Sanyo massage-chair technology (see for United States of America Patent Application Publication US 2005/0137503).

Similar ideas are shown in U.S. Pat. No. 6,067,468, which discloses apparatus for monitoring a person's psycho-physiological condition. In this Patent the running of a program, designed to train the user to control one or more aspects of his or her psycho-physiological state, is controlled by signals representative of a psycho-physiological parameter of the user, for example, galvanic skin resistance. This may be detected by a sensor unit with two contacts on adjacent fingers of a user. The sensor unit is separate from a receiver unit which is connected to a computer running the program. It is the object of all of the known systems to provide accurate feedback to the subject about their current performance. Indeed an many applications, accuracy of the feedback is of paramount importance.

SUMMARY OF THE INVENTION

It is therefore an object of the invention to improve upon the known art.

According to a first aspect of the present invention, there is provided a method of obtaining a desired state in a subject comprising measuring one or more physiological parameters of the subject, calculating, using the measured parameter(s), a value, determining if the calculated value is to be modified, modifying the calculated value, if the determination is that the value is to be modified, and generating an output to the subject, the output being in proportion to the modified value.

According to a second aspect of the present invention, there is provided a system for obtaining a desired state in a subject comprising one or more sensors arranged to measure one or more physiological parameters of the subject, a processor arranged to calculate, using the measured parameter(s), a value, to determine if the calculated value is to be modified, and to modify the calculated value, if the determination is that the value is to be modified, and one or more output devices arranged to generate an output to the subject, the output being in proportion to the modified value.

Owing to the invention, it is possible to provide altered bio-feedback for enhanced emotional experiences. The present method and system relate to the use of bio-feedback in, for example, lifestyle devices. People tend to rely heavily on feedback monitoring for cognitions about their ongoing emotional experiences. There is provided a method to achieve enhanced emotional and/or sexual arousal during usage of the system by implementation of the altered bio-feedback. A feature of the method is the bias/alteration of the sensor signals that are fed back to the user, such that the user starts to believe that their body gets emotionally aroused (or the opposite, i.e. relaxed). Consequently, because of the complex interplay and interaction between psychological and biological factors, what goes on in the mind (e.g. sexual desire) is stimulated.

Until now, the emphasis in bio-feedback systems has been put on providing an accurate feedback about physiological functioning (like for example the galvanic skin response (GSR), electromyography (EMG), heart rate variability (HRV)) to the user. The main aim of this "minding the body" approach, which is well known within, but not restricted to, the healthcare domain, lies in the real-time coaching of the user. Here, the temporal and functional accuracy and resolution of the psycho-physiological sensing method (and consequently the diagnosis) is of major importance. An exemplary application could be to train the user to control one or more aspects of his psycho-physiological state, as described in the prior art Patent referred to above. In that sense, the bio-feedback is used to cause self-behaviour modification in the user. For example this methodology can be used in order to train the user to modify negative behaviour patterns (which is related to the philosophy of mindfullness).

In known virtual reality systems, a realistic simulation of the physical sense of touch is provided via force feedback. The applications of force feedback range widely, from medical training systems for surgeons to teach how hard to press with a scalpel in delicate areas of the human body, to popular joysticks used in computer games, see for example, http://encyclopedia.farlex.com/force+feedback. The use of force feedback is known to provide a more realistic and more intense experience. In these applications, the aim is again to provide accurate feedback.

From an end user point of view, devices in the domain of lifestyle and wellness, such as massage devices with sensors, are not focussed on control over the user's body, as is the case in healthcare applications. Rather, there is an emphasis on enhancing the pleasure of the user by being out of control. The different user needs lead to an a priori different approach for applications. The development of bio-feedback systems with high resolution and high accuracy is therefore not the central issue in this case. The question remains: what could intensify the user's emotional experiences?

So the present system and method are different from the prior art applications. In the domain of lifestyle and wellness as provided by massage devices or devices such as the Aurea television (see http://www.aurea.philips.com), the needs of end users are very different from the users in the healthcare domain, i.e. end users are not primarily interested in the functional resolution of bio-feedback. This is also reflected by the general insight that lifestyle applications preferably do not look too technical. The end user needs in the broad field of lifestyle rather focus on entertainment, fun, and an easy user interface, which is analogous to the values present in the computer games with forced feedback.

This positively inspired approach translates the vision of 'solving problems and dysfunctions' into the vision of 'enhancing the pleasure of the user'.

While accuracy of diagnosis and feedback monitoring is a major concern in the domain of healthcare (user needs focus on health related reasons), in the domain of lifestyle and wellness (for example, massage), the impact of entertainment is far more important. This different emphasis in both fields (differential user needs) leads to completely different applications. It is proposed that the system of altered bio-feedback can be employed to have a big impact in entertainment applications in general, and also more specific devices such as in massage devices.

In the prior art systems, the user receives accurate feedback of their current physiological state (and subsequently their current emotional state if desired), or accurate feedback to the activities being simulated by the system (i.e. the computer game etc.). However, the present invention is designed in order to influence the emotional state of a user in such a way that it may often be more effective to provide stimuli based upon the desired emotional state of the user, which is not necessarily their current emotional state. For example, if a subject wishes to become relaxed, it is not helpful to receive feedback telling them that they are stressed at this moment; a more fruitful approach is to provide feedback along the lines of "you're looking comfortable" and to hope that this suggestion will actually make the subject start to feel at least a little better. Such an approach of dropping a suggestive remark (even if it is clearly not the actual state of the user) can be applied in any emotional situation to induce the subject to realise the desired emotional state. Similarly, systems which simply reflect a user's current emotional state will not be ideal for inducing the desired state in a user.

For this reason, in this invention there is proposed a system, device and method whose primary goal is the explicit alteration of bio-feedback signal(s) in order to obtain a desired state in the subject, for example to enhance the emotional experience of the subject. For the proposed alterations, see below for more detail. The alteration has to be at least plausible. Clearly it is not believable if you were to say to somebody who is clearly depressed that you have never seen them look better. Similarly, the manipulation of the feedback must also be plausible. This will be considered when discussing algorithms for alteration of the feedback.

In one embodiment, the emphasis is put on the intensification of the emotional experience. The aim of intensifying the experience is analogous to the aim of force feedback in computer games. What's different is the explicit biasing of the sensor signals that are fed back to the user. After all, it is the appraisal and/or interpretation of the feedback through the user which makes the difference in emotional experiences (effectively operating as a self fulfilling prophecy). Hereby, suggestiveness and/or evocativeness are very important.

Preferably, the step of modifying the calculated value, if the determination is that the value is to be modified, comprises accessing a modification scheme and modifying the calculated value according to the modification scheme. The scheme may be in the form of a graph or alternatively in the form of a look-up-table (which table is essentially containing the x, y co-ordinates of the graph, as implemented in a processor), defining how the calculated value is to be altered according to the modification applied by the system. This allows a high degree of flexibility in the modification of the value that drives the output to the user, but does so in a manner that is relatively simple to implement. The system can access the modification scheme and perform the modification according to the scheme.

Advantageously, the step of modifying the calculated value, if the determination is that the value is to be modified, comprises amplifying the calculated value. The modification of the value can be a simple amplification according to a multiplication factor. If a modification scheme is used, then this scheme can determine the multiplying factor that is used according to measured value. For example, if the desired state that the user is being pushed towards is an arousal state, then a sensor may be measuring the heart rate of the user, and feeding back an output to the user that is showing their current heart rate. However, the altered feedback delivered by the system will amplify the measured value, to influence the subject to believe that they are more aroused than they really are. Alternatively, the altered feedback can comprise attenuating the calculated value.

In one exemplary embodiment, the step of determining if the calculated value is to be modified comprises comparing the calculated value against a threshold. Additionally, the step of modifying the calculated value, if the determination is that the value is to be modified, can comprise amplifying the calculated value if the calculated value is beyond (either below or above) the threshold. For example, the alteration will amplify the calculated value if it is below a predetermined (fixed or variable=adaptive in time, and either or not personalised) threshold, or in another case the alteration will amplify the calculated value if it is above a predetermined (fixed or variable=adaptive in time, and either or not personalised) threshold. The level of the amplification may depend upon the measured value. For example, if the subject is being pushed towards a desired state that corresponds to a minimum heart rate of 85 beats per minute (BPM), then, if their measured heart rate is below a threshold of 75 BPM, then amplification of the value is performed, for example using a multiplication factor of 1.2.

Ideally, the process further comprises mapping the one or more measured physiological parameters of the subject to a scale and wherein the calculated value comprises a value on the scale. The state of the subject may be calculated in pure objective physical terms, such as heart rate, but may also be considered in subjective terms, such as a relaxation scale. For example, a scale of 1 to 10 may be used, with 1 being most relaxed, and 10 being most aroused. One or more measured physiological parameters are then used to determine the current relaxation state of the subject. These discrete states can be represented to the subject in the output presented by the system. The inventive system provides for the alteration of the output, via modification of the measured values, to provide the altered bio-feedback to the subject. In a further embodiment the system comprises a massage device.

Advantageously, the method further comprises determining the direction of movement of the calculated value, wherein the step of modifying the calculated value, if the determination is that the value is to be modified, is dependent on the direction of movement of the value. This enhancement provides a more effective and adaptable solution. In addition to considering the absolute value when deciding on the modification to be applied, whether this value is increasing or decreasing can be used to determine the nature of the adjustment (i.e. the nature of the modification scheme, or the selection of one out of many predetermined modification schemes, or the online generation of modification scheme) that is applied. For example, if the value is falling then a first graph could be used to determine the modification, and if the value is rising, then a second graph could be used in the modification of the calculated value. In a further embodiment of the system the processor is further arranged to determine the direction of movement of the calculated value, wherein the modifying of the calculated value, if the determination is that the value is to be modified, is dependent on the direction of movement of the value.

BRIEF DESCRIPTION OF THE DRAWINGS

Embodiments of the present invention will now be described, by way of example only, with reference to the accompanying drawings, in which:—

DETAILED DESCRIPTION OF THE EMBODIMENTS

Figure 1:
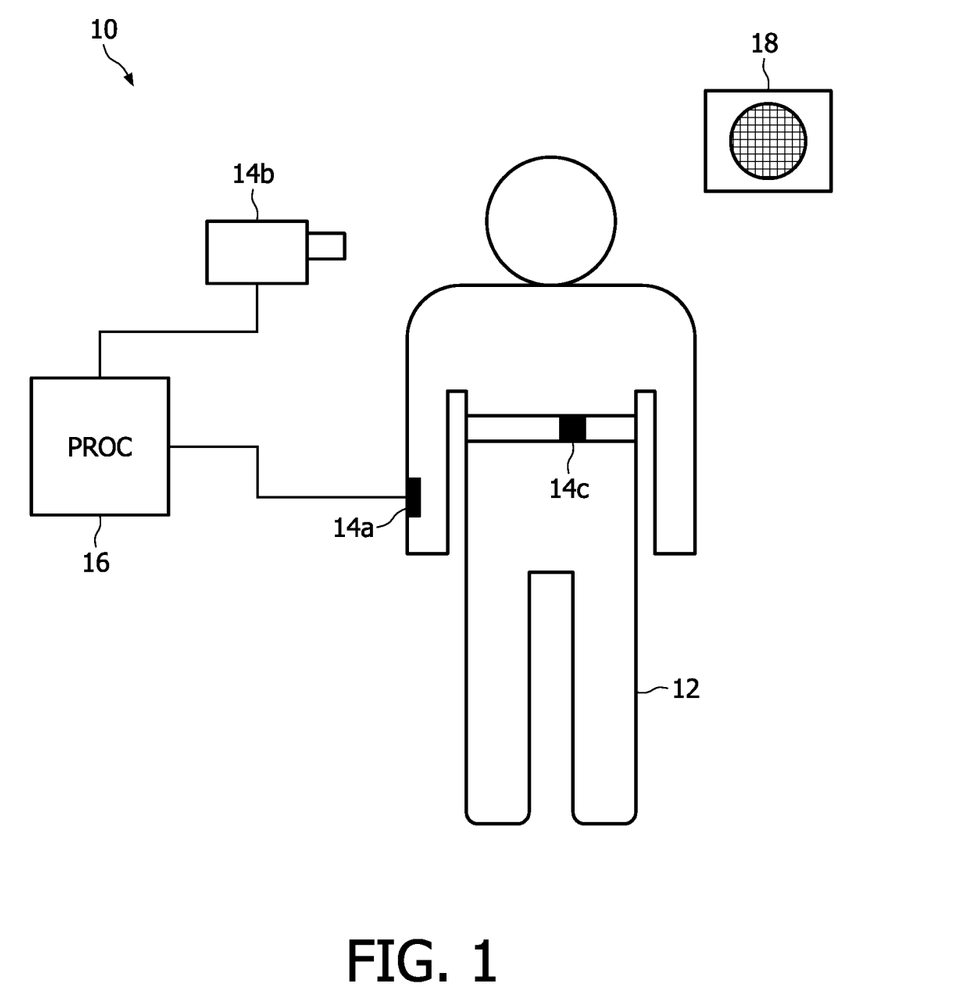
FIG. 1 is a schematic diagram of a system with a subject.

FIG. 1 shows a system 10 for obtaining a desired state in a subject 12. The system 10 comprises sensors 14 which are arranged to measure one or more physiological parameters of the subject 12, a processor 16 arranged to perform, using the measured parameter(s), various calculations, and an output device 18 arranged to generate an output to the subject 12. The system 10 is effectively a feedback system, monitoring the parameters of the subject 12, such as skin temperature and heart rate, and providing feedback to the subject 12 via the output device 18.

The Figure shows the subject 12 being monitored by three separate sensors 14. A first sensor 14a is skin conductivity measuring device, a second sensor 14b is a camera that is monitoring the facial expression and head position of the subject 12, and a third sensor 14c is a wireless heart rate monitor held in place with a strap around the subject's chest. The sensors 14a and 14c can be considered to be direct sensors that are directly measuring physiological parameters of the subject 12, and the sensor 14b is an indirect sensor that is measuring physiological parameters such as the facial expression of the subject 12, and/or the rate of movement of the subject's head. Other indirect physiological sensors that can be used may comprise the manner in which user interacts with a user interface, in dependence upon their current situation, for example the pressure at which the user grips a steering wheel while driving.

The output device 18 is a loudspeaker arranged to provide an output to the subject 18, under the control of the processor 16. A single output device 18 is shown in the Figure, but there is no reason why multiple output devices 18 can't be used, of the same or of a different category. For example, an output device 18 may be provided that constitutes a display device. The subject 12 is provided with a feedback via the audio device 18 and also, in concert, by the associated display device. The output devices 18, or a single output device 18, go to providing the totality of the feedback to the subject 12, under the control of the processor 16, which determines the extent and intensity of the feedback provided to the subject 12, by the device(s) 18.

The system 10 discloses methods to alter the bio-feedback signals that are measured via sensors 14 and are fed back to the user 12 of the system 10, either through atmosphere feedback or device feedback. An essential feature of the system 10 is to measure certain physiological attributes, such as galvanic skin response, local skin temperature, facial expression, heart rate and heart rate variability, respiration, electromyography and apply altered bio-feedback to the user. The processor 16 is controlling the feedback to the user 12, and is arranged to modify the feedback that is provided to the user.

The sensors 14 are provided in order to record one or more physiological signals, body position or facial expression or activity or movement of the user 12. Suitable sensors include measuring the subject's heart rate signal (from which a relaxation state can be derived from the heart rate variation), which can be determined in a variety of ways, for example, with a classical electrical Ag/Ag Cl electrodes measuring the ECG signal, by measuring the ballistocardiogram, for example with a static charge sensitive bed (SCSB), or a piezo foil, or an EMFi-film sensor build into a chair, by measuring the user's oxygen saturation (SPO2), by measuring the (photo)plethysmogram PPG, in the finger, ear, or somewhere else, by using non-galvanic capacitive electrodes, by using a wristwatch like device, by using seismosomnography (SSG), Ultra Wide Band radar, Optical Vibrocardiography, acoustical with a microphone (phonocardiogram), or by using intelligent textile or underwear with built in sensors.

Other physiological based measurement devices include those measuring skin conductivity/perspiration (this is well known as an emotional arousal measurement in the art, and most suitable for judging the users' excitement' level), (skin) temperature, either via a full contact measurement, using a thermocouple, or non-contact infrared sensing thermometer, or brain wave patterns, through EEG. Other sensors could include blood flow sensors (for example light based sensors), and blood gas level sensors (for example measuring oxygen level).

Other physiological parameters that can be measured by the sensors 14 include muscle tension (preferable measured electrically by EMG), and breathing rate, which can be derived from the heart rate variability (as determined from the ECG signal), or could be measured directly on chest/belly by a stretchable band). Alternatively a microphone of a headset or phone could be used to detect acoustically the breathing rate of the subject 12. This signal could also be used to measure user excitement.

The sensors 14 can also be used to perform an audio-based analysis. For example, audio classification means can be used to detect moments of laughing, enthusiastic talking, screaming, crying, significant changes in social contexts and more generally obtain an indication of the emotional state by analysis of the frequency distribution of the audio signal. Similarly, video-based analysis can be used. For example, computer vision can be used to detect and classify social events such as parties, smiling faces etc. In addition, it is possible to use the relative positions of facial features (eyes and mouth relative to the nose) to define the emotional state of the user, for example in the form of a "pleasure vs. arousal level" scale. This has been demonstrated by e.g. the "Empathic painting" project at the University of Bath (http://www.cs.bath.ac.uk/~vision/empaint)

The processor 16 runs software to process the raw physiological signals in real time. Within a certain time window, the minimum and maximum parameter values of the physiological signals are calculated via peak detection. The normalisation procedure allows the processor 16 to evaluate the actual parameter value in relation to the extremes in a certain time interval, and therefore controls for the time variations in baseline parameter values (and thereby provides the system with a personalised, next to an adaptive in time, parameter interval).

The desired emotional state of the subject 12, which is defined by threshold(s) (see below), can therefore be considered as either time invariant, or time variable. The simplest embodiment is to take either one or two fixed threshold values. A more advanced embodiment could be to encapsulate time variations in baseline parameter range, and to handle one or two variable threshold values. Feedback alteration algorithms are run by the processor 16 to determine the modification of the feedback to the subject 12. The heart of the system 10 concerns the alteration of the bio-feedback presented to the user 12. The algorithms which may be used to alter the bio-feedback are described in more detail below.

A first embodiment of the altered bio-feedback system 10 uses a system with a single threshold. The goal of the system 10 is to enhance the subject's emotional experience while using a lifestyle device. In a most simple embodiment of the system 10, the desired ("optimal") state for the user's emotional experience is defined by a boundary (either a lower or upper threshold) for either one or each physiologically measured parameter or alternatively for a combination of two or more physiological parameters. The result of the alteration therefore needs to influence the user 12 to reach a position either above a lower threshold or below an upper threshold and to remain on the correct side of the boundary.

This optimal result is achieved through two fundamental manipulations. The alteration has many qualitatively different possibilities, for example, amplification, attenuation, phase shift (delay), inversion, superposition of a non-measured signal (such as jitter), and a combination of any of these. Quantitatively, the amount of alteration depends on, for example, the slope of the currently measured physiological signal (for example, if the steepness is high, the alteration diminishes, or the alteration depends on the sign of the slope: positive or negative steepness), or the distance of the currently measured parameter value from the threshold value(s).

Figure 2:
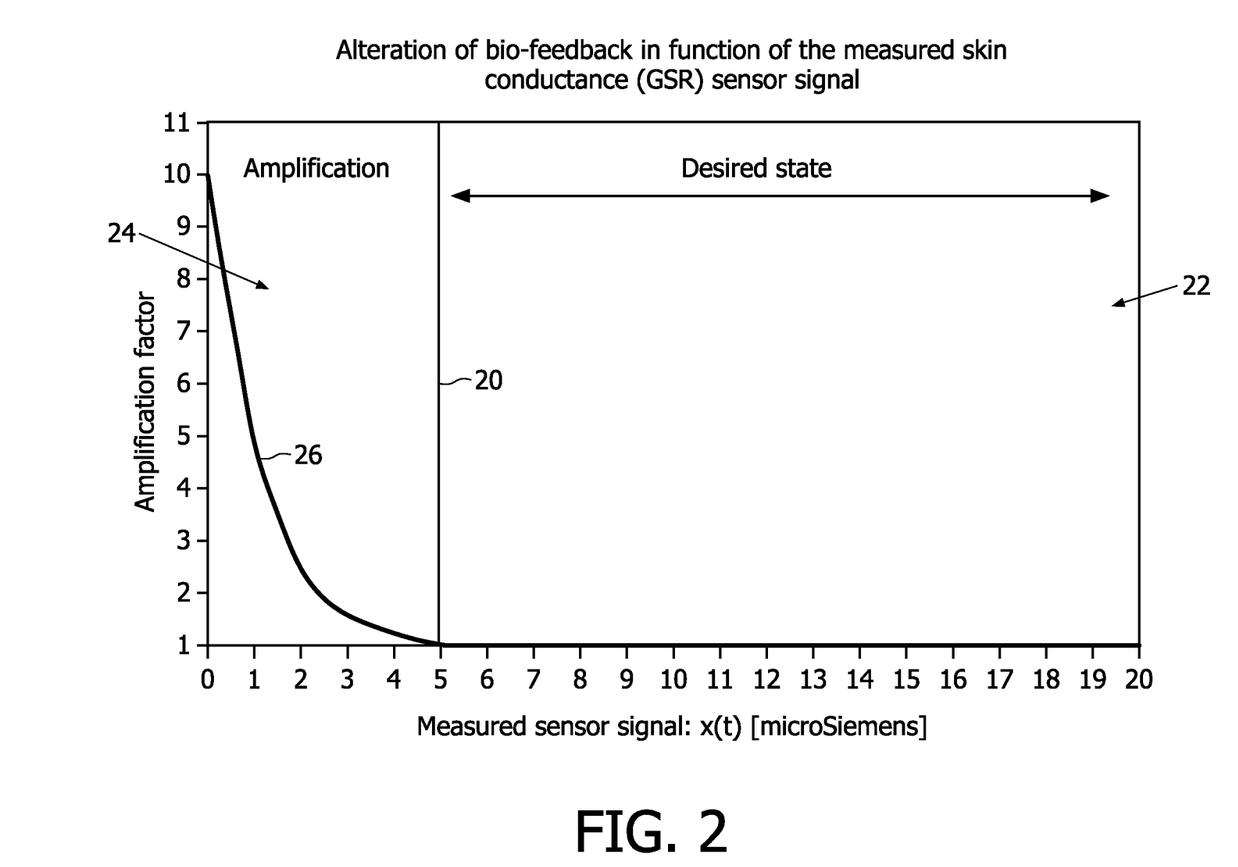
FIG. 2 is a graph showing alteration of bio-feedback using a single, fixed, threshold.

A first example is shown in FIG. 2, which is an illustration to explain the principle of a single, fixed threshold 20, in relation to the processing by the processor 16, in determining whether and how much alteration to apply to the output to the user 12. The measured physiological parameter in this example is skin conductance (GSR) level x(t) is given on the X-axis. The amplification factor of the alteration is given on the Y-axis. The desired emotional state 22 is defined by the single threshold 20, the fixed value (x1)=lower threshold of measured sensor signal, being 5 µS. The threshold 20 separates the desired state 22 of the user 12 from an undesired state 24.

The graph of FIG. 2 illustrates the simple decision rules, if x<x1, then amplify, else if x1≤x then no alteration. The graph 26 can be considered as a modification scheme that is used to modify the output provided to the user 12. The system 10 operates to measure the physiological parameter (skin conductance) of the subject 12. This is then used to calculate a value (here on a scale of 0 to 20 µS). The processor 16 then determines whether to modify this calculated value. In this example, this decision making process is based upon the threshold 20, as detailed above. If it is determined that the calculated value is to be modified, then that value is modified according to the scheme 26, which amplifies the calculated value to create a modified value. The system 10 then generates an output to the subject 12, the output being in proportion to the modified value.

The range of skin conductance (GSR) values lies within 1 to 20 µS as typical values for a wide range of test subjects. It is possible for example to set a lower threshold x1=5 µS. When the currently measured value is lower than the fixed threshold 20, the feedback signal will be amplified. In this example, the amount of amplification depends on the distance between the actual and the desired parameter values. The greater the distance of the calculated value from the lower threshold 20, the steeper the alteration of the feedback, according to the scheme 26. The actual amplification factors are given in the Figure for the situation that the feedback is directly set to the threshold value. Alternative curves could use a somewhat lower value of amplification, which would give the user the impression that they are closer to the desired state than in reality, but still not quite at the desired state. Below, various methods are presented for giving the altered bio-feedback.

Figure 3:
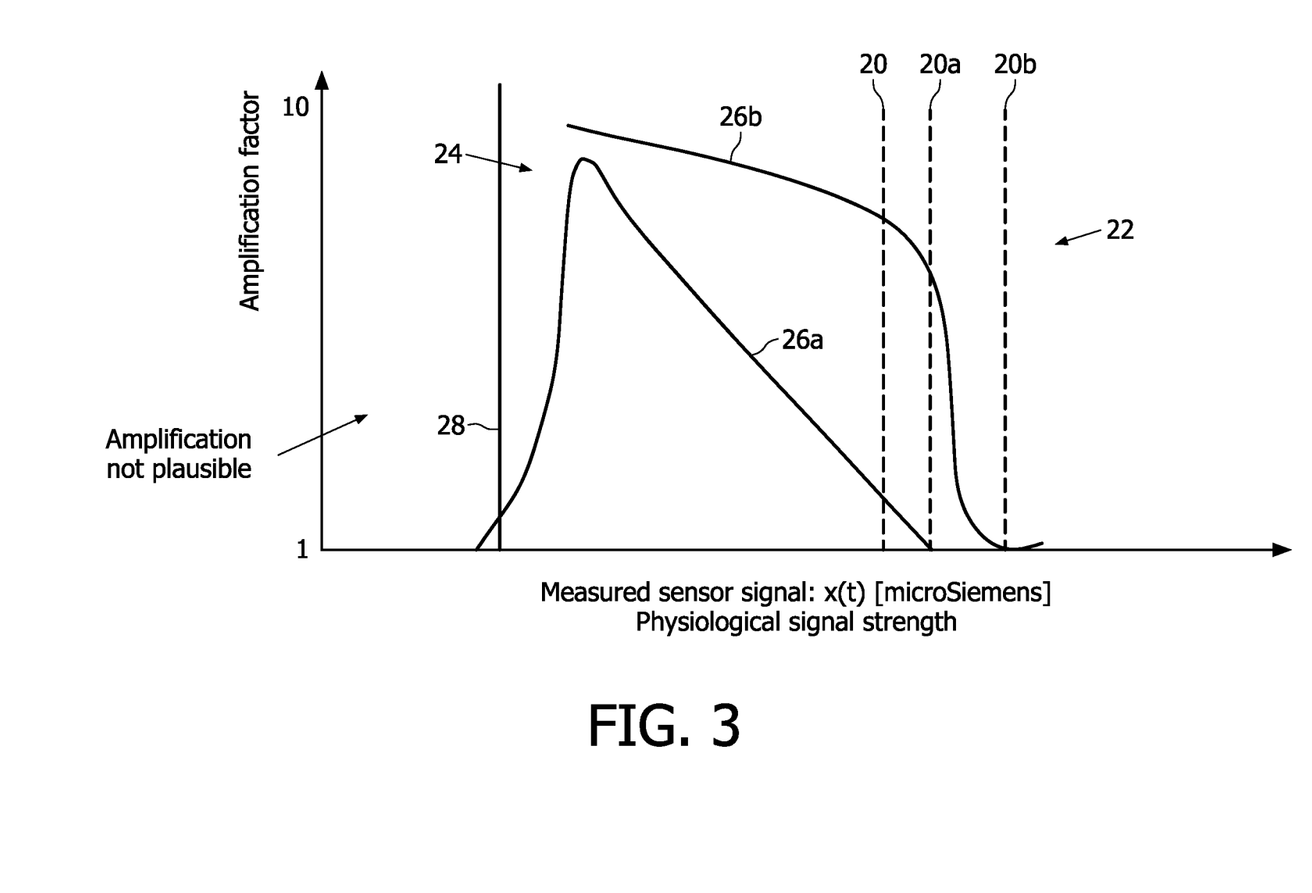
FIG. 3 is an alternative graph showing alteration of bio-feedback, also using a single, fixed, threshold.

A second example is shown in FIG. 3, which is an illustration of a more advanced algorithm, although still using a single threshold 20. When the currently measured skin conductance (GSR) signal x(t) is outside of the desired emotional state, the aim of the altered bio-feedback is to get the person 12 in the right mood, i.e. in the right area 22 of measured parameter values. The algorithm, shown in FIG. 3, gives an example of how to achieve the aim of getting the person 12 above the lower threshold 20.

If the sensed parameter value is too low, feedback will not be altered. In this area, defined by the second threshold 28, amplification is just not plausible (for example, because the person 12 is on the verge of falling asleep, and therefore, at that moment, information about excitement is irrelevant and can even be irritating). This second threshold 28 can for example be set at 50% or less of the lower threshold 20. When the distance between the actually measured value and the threshold 20 is shorter, alteration of feedback starts. The amplification factors are shown in the Figure by the schemes 26. It is the case that depending on the direction of measured sensor value the scheme that is used in the modification of the value is different. The first scheme 26a is used when the value is increasing, and the second scheme 26b is used when the value is decreasing. In particular, scheme 26b will have the effect that if the user begins to approach the lower threshold 20, from within the desired area, 22, they will already get a strongly modified value starting at threshold 20b which will alert them that they are about to leave the desired region and enable them to take action to avoid this.

In this case it should be noted that there is modification of the value whilst the user is (still) in the desired area, 22. This can be realised, within the system, by appreciating that whilst the desired state of the user is represented by a certain value, 20, the threshold for modification may be set at a value either higher (20a, 20b) or lower than the value which defines the desired state.

When the currently measured skin conductance (GSR) signal x(t) lies within the borders of the desired emotional state, the aim of the altered bio-feedback is to keep the person 12 in the right mood, i.e. in the right area 22 of measured parameter values. The algorithm, shown in FIG. 3 (in particular modification scheme 26b), gives an example of how to achieve keeping the person within this area which is defined by one lower threshold 20.

In a further embodiment the altered bio-feedback system 10 operates with a double threshold (lower and upper). In this further system 10, according to the embodiment, the optimal/desired state for the user's emotional experience may be defined by two boundaries (lower+upper threshold) for either each physiologically measured parameter or alternatively for a combination of two or more physiological parameters. The result of the alteration therefore needs to influence the user to reach a position within these two boundaries and then to remain within these two boundaries.

Figure 4:
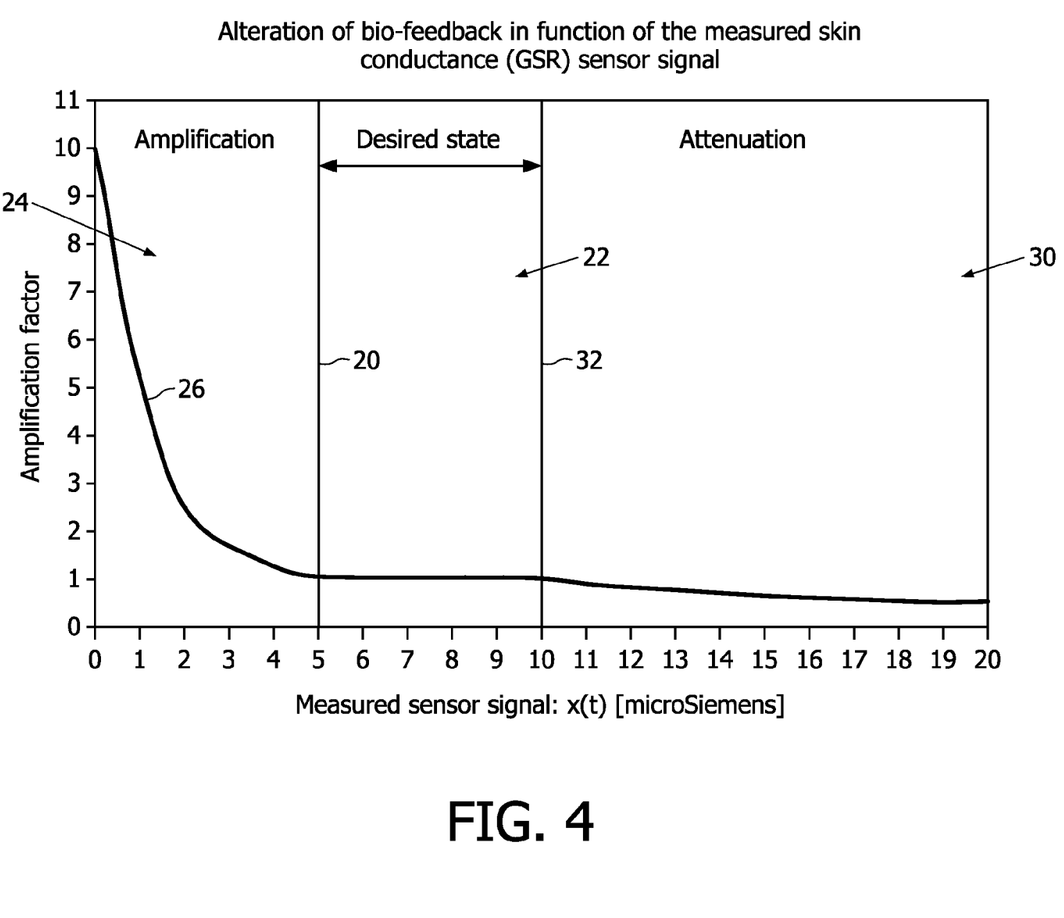
FIG. 4 is a second alternative graph showing alteration of bio-feedback, using two, fixed, thresholds.

A third example is illustrated in FIG. 4, to explain the principle of a double, fixed threshold. The measured skin conductance (GSR) signal x(t) is given on the X-axis. The amplification factor of the alteration is given on the Y-axis. The desired emotional state is defined by two thresholds 20 and 32: the fixed value (x1)=lower threshold of measured sensor signal; the fixed value (x2)=upper threshold of measured signal. The desired state 22 into which the subject is to be led is defined by the lower threshold 20 and the upper threshold 32. If the measured physiological parameter value is below the threshold 20, then the user 12 is in the undesired state 24 (too relaxed), and if the parameter value is above the threshold 32, then the user 12 is in the undesired state 30 (too stressed).

The line 26 defines the modification scheme that is used to modify the value to create the value that is used when generating the output to the subject 12. This graph illustrates the simple decision rules that if $x<x1$ then amplify; and if $x1 \leq x \leq x2$ then no alteration; and if $x>x2$ then attenuate. Therefore is the measured value is below the first threshold 20, then it is amplified, and if the measured value is above the second threshold 32, then it is attenuated.

The range of skin conductance values lies within 2 to 20 µS as a typical value for a wide range of test subjects. There could be, for example, set a lower threshold $x1=5$ µS, and an upper threshold $x2=10$ µS. On the one hand, when the currently measured value is lower than the fixed lower threshold 20, the feedback signal will be amplified. On the other hand, when the currently measured value is higher than the fixed upper threshold 32, the feedback signal is attenuated. In this example, the amount of amplification depends on the distance between the actual and the desired parameter values, as defined by the line 26. The greater the distance of the measured value from the threshold 20, the steeper the alteration of the feedback. The actual amplification factors are given in the Figure for the situation that the feedback is directly set to the threshold (lower and upper) values. Alternative curves could be used (some less amplification, some less attenuation). Clearly, different curves could be used depending upon the direction in which the value approaches the threshold, as was illustrated for a single threshold in FIG. 3.

The thresholds discussed above have all been "fixed" thresholds. It is possible that the threshold, which determines whether the modification is applied to the calculated value, is determined dynamically, for example with reference to the measurement of some other parameter(s). This other parameter could be an external measurement such as the local temperature or could be a different physiological parameter of the subject 12. If more than one threshold is used in the system 10, for example with a second threshold being used to decide not to apply modification (on the grounds of plausibility), then this second threshold could be set as a function of the first threshold, for example being set at 50% of the first threshold.

Figure 5:
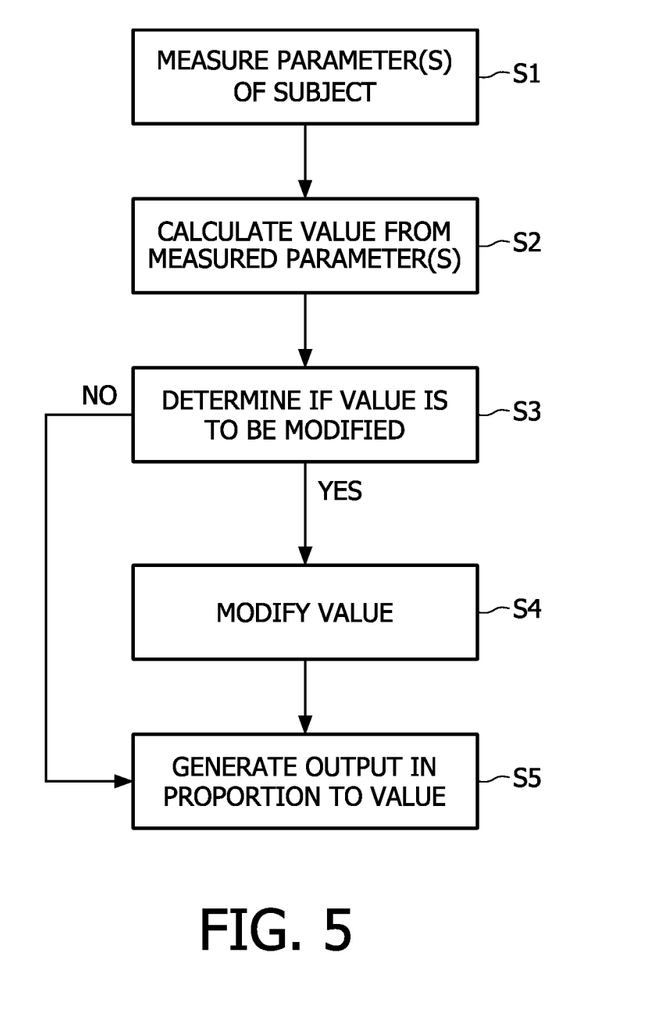
FIG. 5 is a flowchart of a method of obtaining a desired state in a subject.

The method of obtaining the desired state in the subject 12 is summarised in FIG. 5. The method comprises the steps of, firstly at step S1, measuring one or more physiological parameters of the subject 12, and secondly, at step S2, calculating, using the measured parameter(s), a value. In order to derive the value, the procedure, carried out by the processor 16, may also comprise mapping the one or more measured physiological parameters of the subject 12 to a scale and therefore the calculated value comprises a value on the scale. In its simplest form, the value is generated directly from the data that is read by sensors 14. For example, the user's heart rate may be measured by a sensor 14, and the value used will be the user's heart beats per minute. However more complicated processing of the sensor data is possible, to combine data from different sensor 14 and to map that data to scale, which can be considered to be more abstract in nature, such as a relaxation scale.

The next step in the process is step S3, which comprises determining if the calculated value is to be modified. The step of determining if the calculated value is to be modified can comprise comparing the calculated value against a threshold, as discussed above in detail with respect to FIGS. 2 to 4. The processor 16 decides whether to modify the calculated value according to predetermined rules. These can be embodied in one or more algorithms that used by the processor 16 at this stage of the process. This is carried out in real time.

The fourth step in the process is the step S4 of modifying the calculated value, if the determination is that the value is to be modified. The processor 16 applies modification to the calculated value to alter the bio-feedback to the subject 12. The step of modifying the calculated value, if the determination is that the value is to be modified, can comprises accessing a modification scheme 26 and modifying the calculated value according to the modification scheme 26. In the preferred embodiment, the step of modifying the calculated value, if the determination is that the value is to be modified, comprises amplifying the calculated value. If the system is using a threshold to make the determination of whether to apply a modifier to the value, then the step of modifying the calculated value, if the determination is that the value is to be modified, comprises amplifying the calculated value if the calculated value is beyond the threshold.

More complicated levels of processing are possible. For example, the processor 14 may be further arranged to determine the direction of movement of the value on the scale, wherein the step of modifying the calculated value, if the determination is that the value is to be modified, is dependent on the direction of movement of the value.

The final step S5 in the process is the generating of an output to the subject 12, the output being in proportion to the modified value. This final step is applying feedback to the user 12, which may trigger any of the human senses, for example by sound, scent, touch, or sight. Parameters to manipulate are, for example, the intensity or the frequency of the provided feedback signal. Light feedback can be given via a change in colour or a change in brightness. Sound feedback can be given via a change in pitch or a change in amplitude, or if bilaterally presented sound is used: the directional characteristics (binaural inter-aural time and level differences) may vary according to the altered bio-feedback signal. Touch feedback can be given via change in tactile stimulation rhythm or change in pressure of stimulation, or duration of stimulation. Scent feedback can be given via change in fragrance or change in intensity of presented scent. Finally, the feedback may be provided via conscious presentation or via subliminal messages, or a combination of both.

There are many different embodiments and applications in which the system 10 can be embodied. For example, the altered bio-feedback signal can be sent wirelessly to external devices such as a lamp, so that the colour wheel of the lamp can be steered by the feedback controller (the processor 16). Possible outputs to the subject 12 include a movie/animation that is displayed on a television screen.

Another feedback modality is transcutaneous electrical nerve stimulation (TENS) which might be modulated by the feedback controller.

If a subject is lying on bed, the system 10 can be used as a fall-in-sleep aid, the cardio signals are measured, by one of the methods described, but preferably with a ballistocardiogram, so that the subject is free to move. The feedback can be given by modulating lights at a modest level, but also by a relaxing humming sound at modest sound level, which might be modulated by the feedback controller, or a (synthetic) music sound can be used.

During sports activities for example when a subject 12 is participating in gym activities, running, and rowing, the sportsman can get feedback, in particular runners often wear already a HR measurement device. In some activities a device is touched, for example, the steering wheel of a bike, where easily the ECG can be measured, many other gym apparatuses have similar such contacts. Likewise, for sportsmen (boxers, rugby players, etc.), it is important to get in the right mood before a competition. Boxers may set a higher performance if they feel more aroused and less fearful. Actors can set a more realistic scene (e.g. anger emotion) if they really feel the emotion they are about to express. In that sense, the altered bio-feedback can be used as a training tool. At the office working with a PC, the user can be made more relaxed.

Figure 6:
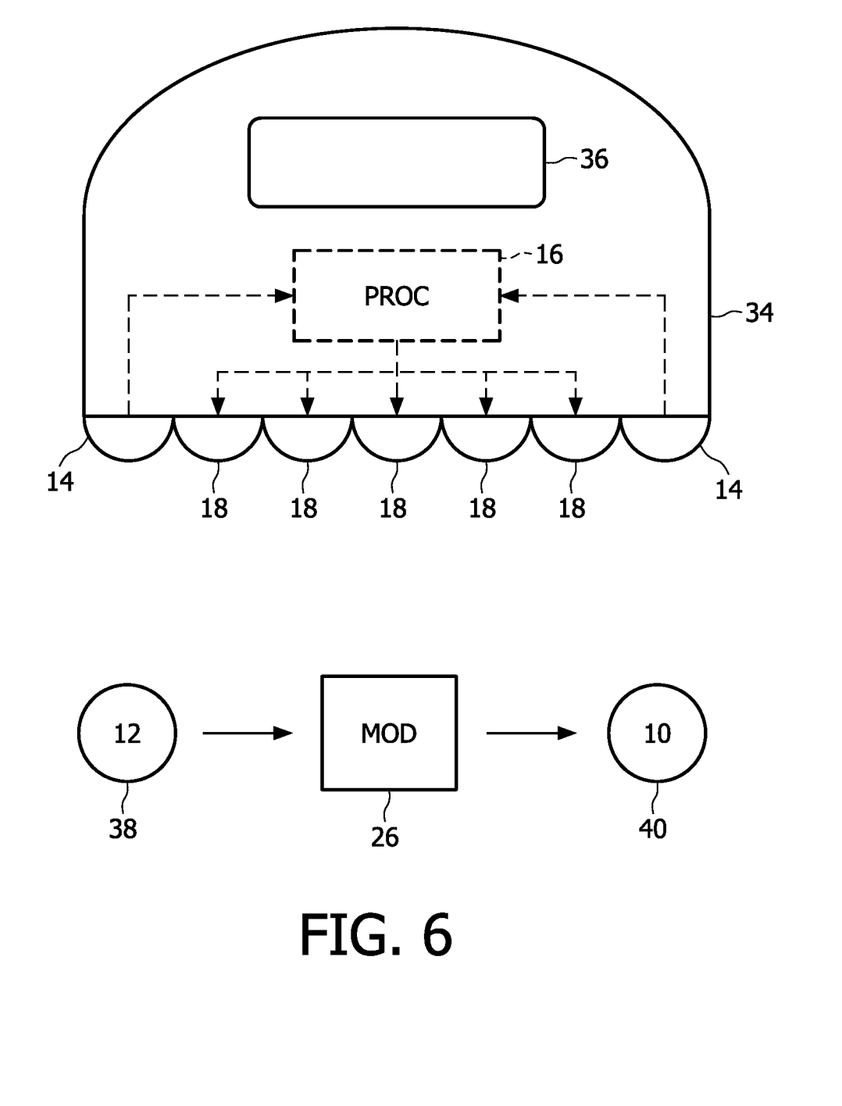
FIG. 6 is a schematic diagram of a second embodiment of the system.

In a preferred embodiment, shown in FIG. 6, the system further comprises a hand held massage device 34, which is provide with a handle hole 36 for the subject 12 to use. Optionally, such a massage device may further comprise the means for measuring the physiological parameters of the subject. Many hand held massage devices are available on the market, usually comprising a plastic casing and one or more vibration inducing motors. An example of a massage device comprising physiological sensors, in this case GSR sensors, is given in U.S. Pat. No. 4,173,217.

The embodiment of FIG. 6 includes the sensors 14 built in to the device, which could measure skin temperature, or some other physiological parameter of the subject 12. The processor 16 receives the measurements from the sensors 14, and controls the output of the output devices 18, which are intended to contact the skin of the subject 12. The processor 16 is configured to provide altered bio-feedback to the subject 12, as shown schematically in the lower half of the Figure. In this case, the calculated value 38 is modified according to the scheme 26, to produce the modified value 40. In this example, the processor 16 has attenuated the value 12 to 10, and the feedback provided by the output devices 18 will be in proportion to this modified value 40.

The invention claimed is:

1. A method of obtaining a desired state in a subject comprising:
    measuring, via one or more sensors, one or more physiological parameters of the subject;
    calculating, via a processor, using the measured one or more physiological parameters, a value representative of an actual state of the subject;
    comparing, via the processor, the calculated value against at least one threshold that comprises a boundary configured to separate the desired state from an undesired state, and determining that the calculated value is to be modified in response to a comparison indicating that the calculated value occurs in the undesired state;
    modifying, via the processor, the calculated value to produce a modified value in response to a determination that the calculated value is to be modified, wherein modifying the calculated value to produce the modified value comprises altering the calculated value in a manner configured to influence the subject to obtain the desired state; and
    generating, via the processor and at least one output device, a biofeedback signal to be output to the subject and configured to trigger at least one of the subject's human senses, wherein the output bio-feedback signal is in proportion to the modified value, wherein responsive to determining that the calculated value is to be modified, the step of modifying the calculated value to produce the modified value further comprises altering the calculated value (i) qualitatively to manipulate an intensity of the bio-feedback signal, wherein qualitatively includes amplification, attenuation, phase shift, inversion, and superposition of a non-measured signal, and (ii) quantitatively to manipulate a frequency of the bio-feedback signal, wherein quantitatively includes an amount of alteration that depends on a slope of a currently measured physiological parameter with respect to a previously measured physiological parameter and a distance of the currently measured physiological parameter from a threshold value.

2. The method according to claim 1, wherein the step of modifying the calculated value to produce the modified value in response to a determination that the calculated value is to be modified, further comprises accessing a modification scheme and modifying the calculated value to produce the modified value according to the modification scheme.

3. The method according to claim 2, wherein the modification scheme is in the form of a graph or look-up table.

4. The method according to claim 1, further comprising mapping, via the processor, the one or more measured physiological parameters of the subject to a scale and wherein the calculated value comprises a value on the scale.

5. A system for obtaining a desired state in a subject comprising:
    one or more sensors arranged to measure one or more physiological parameters of the subject;
    a processor arranged to calculate, using the measured one or more physiological parameters, a value representative of an actual state of the subject, to compare the calculated value against at least one threshold that comprises a boundary configured to separate the desired state from an undesired state, to determine that the calculated value is to be modified in response to a comparison that the calculated value occurs in the undesired state, and to modify the calculated value to produce a modified value in response to a determination that the calculated value is to be modified, wherein modifying the calculated value to produce the modified value comprises altering the calculated value in a manner configured to influence the subject to obtain the desired state; and
    one or more output devices operatively coupled to the processor and arranged to generate a biofeedback signal to be output to the subject and configured to trigger at least one of the subject's human senses, wherein the output bio-feedback signal is in proportion to the modified value, wherein responsive to determining that the calculated value is to be modified, the step of modifying the calculated value to produce the modified value further comprises altering the calculated value (i) qualitatively to manipulate an intensity of the bio-feedback signal, wherein qualitatively includes amplification, attenuation, phase shift inversion, and superposition of a non-measured signal, and (ii) quantitatively to manipulate a frequency of the bio-feedback signal, wherein quantitatively includes an amount of alteration that depends on a slope of a currently measured physiological parameter with respect to a previously measured physiological parameter and a distance of the currently measured physiological parameter from a threshold value.

6. The system according to claim 5, wherein the processor is further arranged, when modifying the calculated value to produce the modified value in response to a determination that the calculated value is to be modified, to access a modification scheme and to modify the calculated value according to the modification scheme.

7. The system according to claim 6, wherein the modification scheme is in the form of a graph or look-up table.

8. The system according to claim 5, wherein the processor is further arranged to map the one or more measured physiological parameters of the subject to a scale and wherein the calculated value comprises a value on the scale.

* * * * *